US 12,161,772 B1

(12) United States Patent
Prax

(10) Patent No.: US 12,161,772 B1
(45) Date of Patent: Dec. 10, 2024

(54) FLUID DISINFECTANT DISPERSANT SYSTEM

(71) Applicant: Xavier R. Prax, Willoughby Hills, OH (US)

(72) Inventor: Xavier R. Prax, Willoughby Hills, OH (US)

( * ) Notice: Subject to any disclaimer, the term of this patent is extended or adjusted under 35 U.S.C. 154(b) by 732 days.

(21) Appl. No.: 17/333,923

(22) Filed: May 28, 2021

Related U.S. Application Data

(60) Provisional application No. 63/031,544, filed on May 28, 2020.

(51) Int. Cl.
| | |
|---|---|
| *A61L 2/22* | (2006.01) |
| *A61L 2/20* | (2006.01) |
| *A61L 2/26* | (2006.01) |
| *B60S 1/64* | (2006.01) |
| *B64F 5/30* | (2017.01) |

(52) U.S. Cl.
CPC .................. *A61L 2/22* (2013.01); *A61L 2/20* (2013.01); *A61L 2/26* (2013.01); *B60S 1/64* (2013.01); *B64F 5/30* (2017.01); *A61L 2202/121* (2013.01); *A61L 2202/123* (2013.01); *A61L 2202/14* (2013.01); *A61L 2202/15* (2013.01); *A61L 2202/16* (2013.01); *A61L 2202/25* (2013.01)

(58) Field of Classification Search
CPC ..... A61L 2/22; A61L 2/20; A61L 2/26; A61L 2202/25; A61L 2202/15; A61L 2202/14; A61L 2202/121; A61L 2202/123
See application file for complete search history.

(56) References Cited

U.S. PATENT DOCUMENTS

| | | | | |
|---|---|---|---|---|
| 5,687,573 | A * | 11/1997 | Shih ................... | B60H 1/00478 62/262 |
| 2014/0106007 | A1* | 4/2014 | Shanahan .............. | A01N 59/00 424/661 |
| 2015/0037206 | A1* | 2/2015 | Akutsu ................... | A61L 9/046 422/292 |
| 2015/0190538 | A1* | 7/2015 | Olvera ..................... | A61L 2/24 250/455.11 |

* cited by examiner

*Primary Examiner* — Lessanework Seifu
(74) *Attorney, Agent, or Firm* — Invention To Patent Services; Alex Hobson

(57) ABSTRACT

A disinfecting system is configured for disinfecting an enclosure or a plurality of enclosures and includes a distribution conduit having a plurality of delivery conduits and dispensing ports. Valves enabling a flow of disinfectant to be controlled to the dispensing ports and these valves may be manual or may be electronic valves that are controlled remotely. An enclosure may be a vehicle such as an automobile, or aircraft, a lavatory and/or a shipping container. Each enclosure may comprise a portion of the disinfecting system, such as a dispensing port. A plurality of lavatories may each comprise one of the plurality of dispensing ports. An aircraft may comprise delivery conduits and a plurality of dispensing port and the distribution conduit may be coupled thereto to enable disinfecting of the aircraft between flight. The disinfectant may be an aerosol of a mist of liquid droplets.

17 Claims, 7 Drawing Sheets

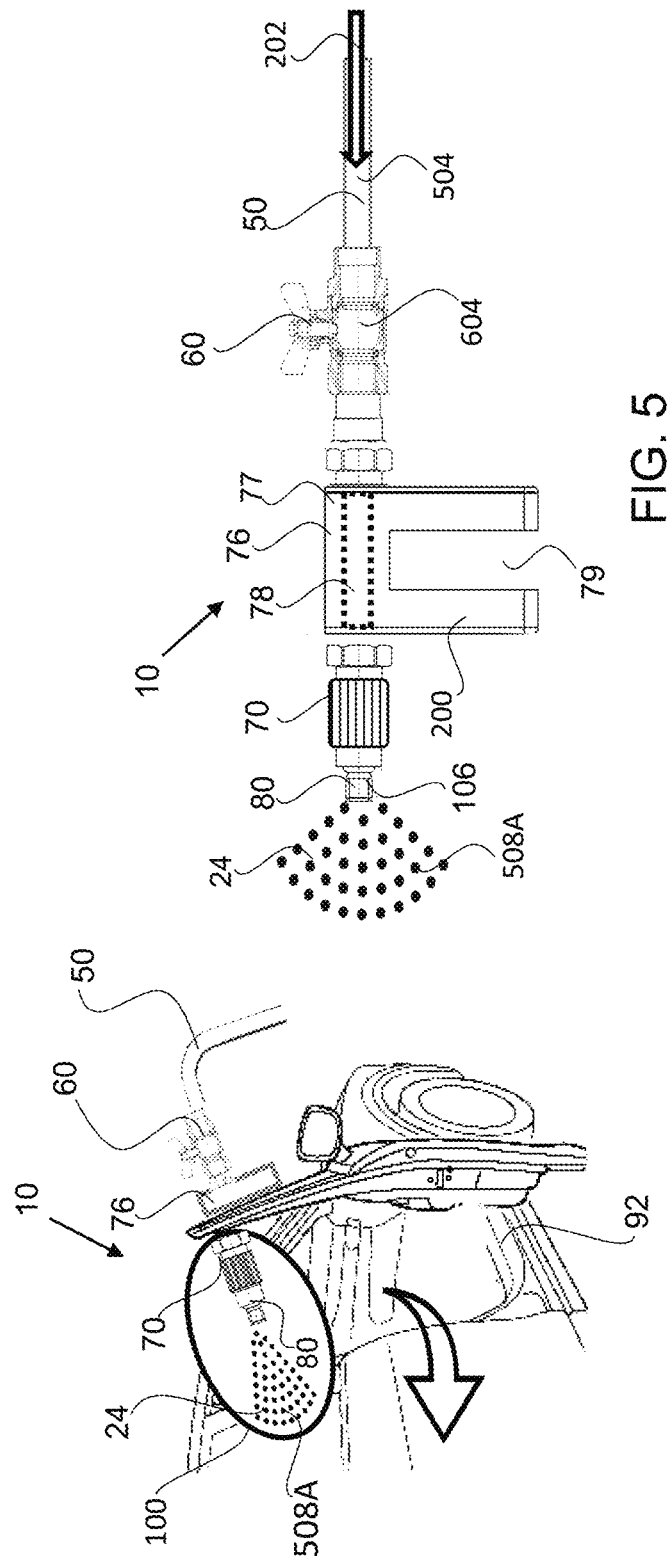

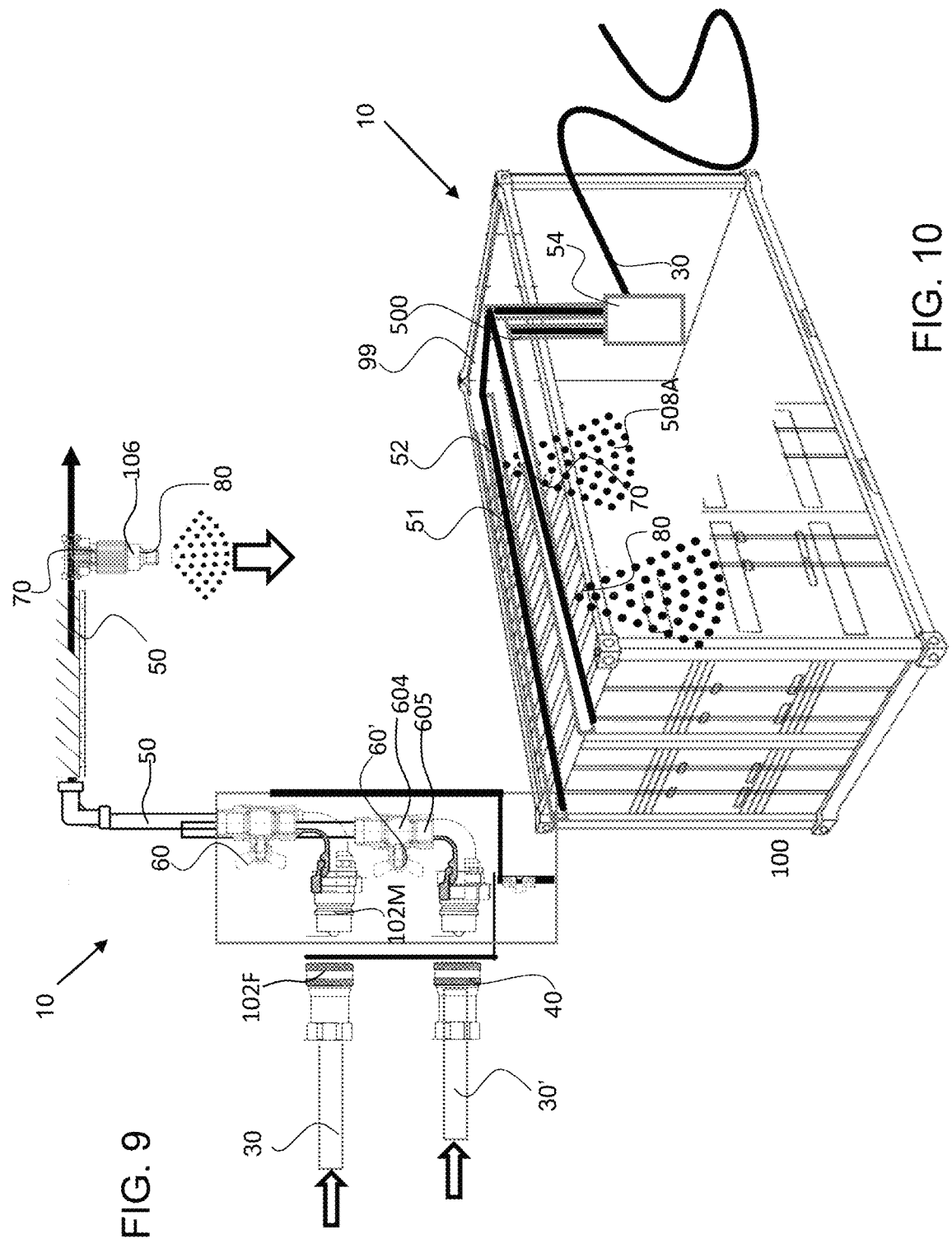

FLUID DISINFECTANT DISPERSANT SYSTEM

CROSS REFERENCE TO RELATED APPLICATIONS

This application claims the benefit of priority to U.S. provisional patent application No. and 63/031,544, filed on May 28, 2021; the entirety of which is hereby incorporated by reference herein.

BACKGROUND OF THE INVENTION

Field of the Invention

The invention relates a disinfecting and sanitizing system configured with a plurality of dispensing ports to enable disinfecting of a large enclosure or a plurality of discrete enclosures and enclosures that have integrated delivery portions that are configured to couple with a disinfectant delivery system.

Background

Cleaning, disinfecting and sanitizing are an ongoing and continuous practice within singular and/or independent module unit(s) including, but not limited to, intermodal freight transportation units, both refrigerated units a.k.a. (reefer) and/or dry shipping containers also within public transportation such as subway car(s), buses, aircrafts and portable toilets, henceforth referring to these units as "Individual module units" or enclosures or delivery units. Oftentimes these cleaning, disinfecting and sanitizing practices go unchecked and may be understaffed, not performed on a regular basis and/or are not upheld to a sufficient standard or are unregulated.

These independent module units have surfaces that are exposed to extreme temperature fluctuations, high moisture levels various, odors, bacteria, virus, germs and mold. Intermodal shipping enclosures can contain moisture that condenses due to temperature fluctuations and this condensed water can create an environment for bacteria to thrive, can produce mold, mildew, bacteria and algae growth. Furthermore, this condensed moisture can result in spoilage of food products and other damaged goods, such as drywall, for example. Shipping from colder to warmer climates, is one of the most high-risk and expensive endeavors, which can result in the losses of billions of dollars globally.

With the global Coronavirus (COVID-19) pandemic along with other contagious germs and viruses surface disinfecting is becoming paramount and require intermittent disinfecting of surfaces.

The International Plant Protection Convention, was a 1951 multilateral treaty overseen by the Food and Agriculture Organization that aimed to secure coordinated, effective action to prevent and to control the introduction and spread of pests of plants and plant products. This convention established GLOBAL EQUIPMENT CLEANING GUIDELINES for both DRY and refrigerated container a.k.a. "reefer" intermodal shipping containers. These stringent cleaning guidelines and criteria include full disinfectant washing and/or steam cleaning so to kill proliferating microbes between each and every turn around use of the reefer.

Current sanitation, disinfecting, sanitizing and/or washing methods are conducted within these various single or independent unit(s) manually and/or solo unit robotically which requires 12 minutes for a 20 ft and 24 min for a 40 ft container per one container at a time consuming and expensive, as well a using toxic chemicals which are environmentally unsafe and unhealthy for humans. For example, robotically sanitizing and disinfecting a one hundred forty foot container unit(s) would take 40+ hours.

So whether the Intermodal transportation and shipment of goods on a ship, aircraft, shipping containers local or overseas and/or in static public spaces such as ambulance, mass transportation, rental cars, portable restrooms and currently there is no fast economical fluid atomizing system that effectively disperses disinfectants and sanitizers to eliminate bacteria, fungi, viruses and algae on a wide range of these indoor settings. The current methodology is either using a portable a solo manual fogging device, a solo manual operated power washer or manual hand washing.

SUMMARY OF THE INVENTION

The invention is directed to a disinfecting system configured with a plurality of dispensing ports to enable disinfecting of a large enclosure or a plurality of discrete enclosures. An exemplary disinfecting system is configured for disinfecting an enclosure or a plurality of enclosures and includes a distribution conduit having a plurality of delivery conduits and dispensing ports. Hose lines with coupling hardware accessories and dry fog misting nozzles with valves route the fluid and enable a flow of disinfectant and/or sanitizer to be controlled to the dispensing ports and these valves may be manual or may be electronic valves that are controlled remotely. An enclosure may include an integrated delivery portion that is coupled with the enclosure and may be detachably attachable to the enclosure or may attached and fixed to or with the enclosure and comprise a coupling for coupling to a delivery conduit of the disinfecting system. be a vehicle such as an automobile, or aircraft, a lavatory and/or a shipping container (delivery unit). Each enclosure may comprise a portion of the disinfecting system, such as a dispensing port. A plurality of lavatories may each comprise one of the pluralities of dispensing ports. A mobile unit may comprise delivery conduits and a plurality of disinfectant dispensing locations and the distribution conduit may be coupled thereto to enable disinfecting of the mobile unit between a rotation of personal, passenger, cargo and/or storage use. The disinfectant, other fluids and/or emerging fluid technologies may be distributed as an aerosol dry fog and/or electrostatic dispersant of a mist of liquid droplets to create a dry fog with microns of 15, +/−5.

An exemplary disinfecting system comprises a disinfecting pressure pump unit to the network of fluid lines and nozzles that contains and provides delivery of the disinfectant solutions into the solo or plurality of individual units. The disinfectant flows from the source through a distribution conduit. A plurality of couplings connect the distribution conduit with a plurality of delivery conduits. The deliver conduit(s) extends to a dispensing port for dispensing the disinfectant into an enclosure. Each of a plurality of discrete enclosures may include one or more of the dispensing ports. For example, a series of lavatories may each have one delivery port configured to dispense the disinfectant down over the lavatory. A larger enclosure, such as an aircraft, may include an integrated delivery conduit that extends along the aircraft to a plurality of delivery ports coupled thereto, to enable disinfecting of this larger enclosure. The distribution conduit may be coupled with an integrated coupling that couples the delivery conduit with the integrated delivery conduit to provide the flow of disinfectant through the aircraft.

A coupling may be a branched coupling, wherein the distribution conduit branches to each of a plurality of delivery conduits, or the couplings may be configured in series from the distribution conduit. A coupling may comprise a male and a female portion and the coupling may be a quick connect coupling. A coupling may be a quick connect type coupling that enables quick manual attachment of a distribution conduit and/or delivery conduit.

An exemplary enclosure may be a vehicle, aircraft, watercraft, shipping container, public transportation vehicle such as a train or subway train, parcel delivery vehicle, bus, rental car fleet, for hire vehicles, portable toilets, temporary field hospital, military facility and the like. An enclosure may have an integrated delivery conduits and ports, as described herein for the aircraft. This integrated deliver system may be configured for buses and larger ships as well. Smaller vehicles may also have an integrated delivery portion that may be detachably attach with the dispensing ports and/or delivery conduit for disinfecting. A personal vehicle may for example couple a dispensing port to an opening in a window to dispense disinfectant into the vehicle. A window adapter may have a channel that extends over the window to secure the dispense port to dispense disinfectant into the vehicle. An adapter conduit may extend from the delivery conduit, along the window adapter to the dispense port. A fleet of taxis or a paid transport service vehicle may have an integrated deliver portion with delivery conduits and dispensing ports configured and fixed in each of the vehicles. These vehicles may simply connect to the distribution conduit by the coupling and initiate the flow of disinfectant into the vehicle. This service may be provided at a company facility, airport or at gas stations for example, much like a pay for tire inflation service.

In an exemplary embodiment, the enclosure is a lavatory of a plurality of lavatories. The lavatories may be configured with an integrated delivery portion and a row of lavatories, such as commonly found at large public events, may be coupled with a distribution conduit to enable periodic disinfecting of all of the enclosures. In an exemplary embodiment, each lavatory has a door sensor and the disinfectant is dispensed when the door is closed, such as between uses or after a pre-determined number of uses. This type of practice would greatly reduce the spread of pathogens.

An exemplary enclosure is a shipping container which may comprise an integrated deliver portion having the delivery conduit and dispensing port(s) integrated into the shipping container. Shipping containers can carry a wide variety of goods including, but not limited to, food such as fruits and vegetables. The cargo may be sanitized upon loading or between loads to ensure no cross contamination.

The valves that control the flow of disinfectant from the source to the dispensing valves may be manually controlled, or may be electronic valves that is opened and close based on a control signal. The electronic valves may be wired with a controller or may have a wireless signal receiver that enables control via a wireless signal delivered by the controller, which may be a remote controller. A valve may be configured with the coupling such as on the delivery conduit side of the coupling, or on the distribution conduit side of the coupling, or proximal to the dispensing port. An integrated delivery portion may be configured with the valve or it may be on a distribution conduit that is configured to couple with the integrated delivery portion. A controller in the vehicle or enclosure may control the opening and closing of the valve when the valve is configured with an integrated delivery portion.

An exemplary disinfectant comprises an EPA and/or FDA registered, approved, non-rinse disinfectants and non-surfactant disinfectants to eliminate bacteria, fungi, viruses and alga solution. An exemplary disinfectant comprises Hypochlorous Acid (HOCL). An exemplary disinfectant comprises ethylene gas for fruits and vegetables.

In an exemplary embodiment, the invention provides a method for multi-linking individual enclosures intermodal and/or static for time and labor saving disinfecting and/or semi-automated power washing.

An exemplary disinfecting system may produce a flow of disinfectant into an enclosure that effectively sanitizes and/or disinfects the enclosure. A disinfectant may be an provided as an atomize or aerosolized mist or fog, or as a dry-fog, or as a liquid spray for washing over the interior of the enclosure. The dispensing port may incorporate a high pressure dry fog and/or electrostatic nozzle(s) to produce a highly dispersed disinfectant. In an exemplary embodiment, an electrostatic dry fog nozzle may be used for dispensing the disinfectant from the delivery port.

This method and/or system uses a single external high pressure fluid pump system to a multiple of predetermined and/or select Individual module, intermodal and/or static unit which quick couples via a network of linked and/or daisy chain of dormant hoses. The pressure may be high, such as PSI 1000+/−500 and including the pressure values provided adjusted for the length of fluid delivery lines.

Disinfectant as used herein includes but is not limited to cleaning solutions, disinfectants and a non-rinse novel disinfectant that are well suited for the food industry. A disinfectant system may also supply a flow of rinse solution to rinse disinfectant from the surface within an enclosure. A cleaner may have a surfactant and/or other antioxidant compounds. A disinfectant may clean and kill viruses or pathogens. An exemplary disinfectant kills or neutralizes 95% or more of viruses and pathogens on surfaces, or as much as 99% or more. A disinfectant may comprise an hypochlorous acid (HOCL) and/or high pH solution having a pH 12.5=+/−1.5, such as ECA water and any emerging fluid technologies. An exemplary disinfectant may also include a gas, such as ethylene, ozone, oxygen gases and the like.

"Application of electrolyzed water in the food industry", Yu-Ru Huang a, Yen-Con Hung b, Shun-Yao Hsu c, Yao-Wen Huang d,e, Deng-Fwu Hwang d, *a Department of Food Science, National Penghu University, Penghu, Taiwan, ROC b Department of Food Science and Technology, College of Agriculture and Environmental Sciences, University of Georgia, Griffin, GA 30223-1797, USA c Graduate Institute of Food Science and Technology, National Taiwan University, P.O. Box 23-14, Taipei 106, Taiwan, ROC d Department of Food Science, National Taiwan Ocean University, Keelung, Taiwan, ROC e Department of Food Science and Technology, Center for Food Safety, University of Georgia, Athens, GA 30602-7610 https://meridian.allenpress.com/jfp/article/71/9/1934/172226/Electrolyzed-Water-and-Its-Application-in-the-Food.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 4 shows a perspective view of an exemplary disinfecting system coupled with an opening in a window of a vehicle.

FIG. 5 shows a side view of a portion of an exemplary disinfecting system including the delivery conduit coupled with a valve and a dispensing port having a nozzle for spraying the disinfectant.

FIG. 9 shows a side view of an exemplary integrated delivery portion having a delivery conduit and a dispensing port with a nozzle to create a spray of disinfectant.

FIG. 10 shows a perspective view of a shipping container having an integrated delivery portion that enables a distribution conduit to be coupled to a coupling fixed to the shipping container to provide a flow of disinfectant therein.

Figure 1:
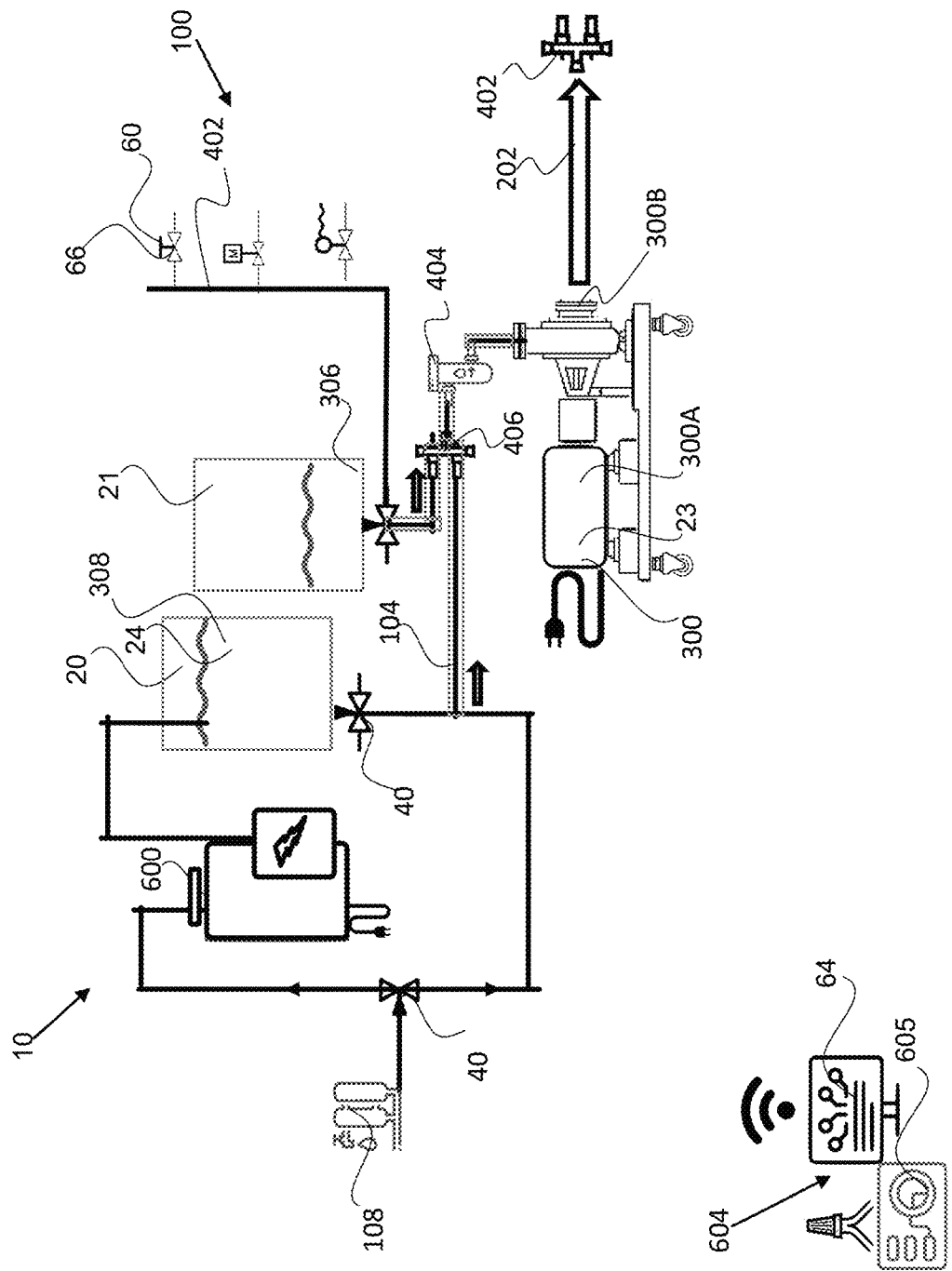
FIG. 1 shows a diagram of an exemplary high pressure fluid pumping "non-binary" system mechanic components, fluid(s) and non-compulsory operating systems interfacing. Shown with optional on-site ECA Generator

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Reference will now be made to the figures wherein like structures will be provided with like reference designations. It is understood that the figures are diagrammatic and schematic representations of some embodiments of the invention, and are not limiting of the present invention, nor are they necessarily drawn to scale.

TABLE 1

| Ref. # | Reference Number Table |
|---|---|
| | Reference number list: |
| 10 | Disinfecting system |
| 20 | Disinfectant source |
| 21 | Dispersant tank |
| 23 | Pump |
| 24 | Disinfectant |
| 26 | Disinfectant soultion |
| 30 | Distribution conduit |
| 32 | Distribution conduit extension |
| 40 | Coupling |
| 42 | Branched coupling |
| 50 | Delivery conduit |
| 51 | Integrated delivery conduit |
| 52 | integrated delivery portion |
| 54 | Integrated coupling |
| 60 | Valve |
| 64 | Controller |
| 66 | Signal receiver |
| 70 | Dispense port |
| 76 | Window adapter |
| 77 | Seal portion |
| 78 | Adapter conduit |
| 79 | Channel |
| 80 | Nozzle |
| 90 | Enclosure |
| 94 | Aircraft |
| 96 | Portable toilets |
| 97 | Door |
| 98 | Door sensor |
| 99 | Shipping Container |
| 100 | Delivery units |
| 102M | Connect coupling Male |
| 102F | Connect coupling female |
| 106 | Atomizing Nozzle |
| 108 | Water Source |
| 202 | Flow direction |
| 300 | High pressure fluid delivery unit |
| 300A | Electric motor |
| 300B | Fluid pump |
| 306 | Dispersant |
| 308 | Disinfectant Storage tank |
| 400 | Seat |
| 402 | Manifold |
| 404 | Fluid filter |
| 502 | Primary external fluid delivery hose |
| 504 | Secondary external fluid delivery hose(s) |
| 508A | Atomizing disinfectant |
| 600 | ECA on-site solutions generator optional |
| 604 | Electronic valve |
| 605 | Wireless signal receiver |

Embodiments of the present invention method for multi-linking and/or Individual, Intermodal and/or static unit(s) for surface and/or content disinfecting refers to various to service a wide array of Individual unit(s) ranging from, but not limited to, Intermodal and/or static shipping containers, mass and public transportation, land and sea, refrigerated and non-refrigerated shipping containers, temporary structures and portable toilets.

As shown in FIG. 1, an exemplary disinfecting system 10 comprises a disinfectant source 20, such as a disinfectant tank 21. The disinfectant 24 may be pumped through the system by a pump 23. The disinfectant is pumped through control valves 60. The valves may be controlled remotely by a controller 64 that sends a wireless signal. The valve may have a signal receiver 66 for receiving the wireless signal to open or close the valve. The valve may also be manual or may be wired to a control system or hub of the control system.

FIG. 1 illustrates a standard high pressure "Autonomous" fluid pumping system comprising a pumping system on/off control fluid routing valve(s) configured in a manifold 402, with a plurality of extensions to separate disinfection ports. This valve may be manual, motorized, wireless wherein it is controlled by a wireless signal such as Bluetooth. The manifold 402 may be controlled manually, through a motorized mechanism, through a wireless signal, such as by Bluetooth and which may interface with a "non-compulsory operating systems", or controller 64. The valves and manifolds may also be hard wired for motorized function(s) or may be manually controlled. This high-pressure fluid pumping system with all of it components may include but not limited to, the high pressure fluid delivery unit 300 that may include, but are not limited to a electric motor 300A, fluid pump 300B, external fluid storage and dispersant 306. The disinfectant delivery units 100, which may be individual, intermodal and/or static unit(s) including, enclosures, vehicles, bathrooms, portable bathrooms, storage and transport enclosures and the like. The delivery units are configured to receive the disinfectant 24, which may be a fluid, for a disinfecting, sanitation and/or cleaning from the exemplary disinfecting system. The disinfectant may include, but is not limited to a range of eco-friendly disinfectants. The disinfectant may be produced and provided to the system by an Electro-chemical activation "ECA" generator(s) 600, such as available from ZONEMIST SYSTEMS, Sarasota, Florida, which creates "on-site" high volume production solutions that greatly reduces trucking, labor and handling costs as well provides a low cost of ingredients "water, salt, electricity". These ECA units produce a hypochlorous acid, an anolyte and/or high alkaline pH 12.5=+/−1.5, a catholyte disinfectant 24. The hypochlorous acid are currently used for disinfectant, sanitation of all types of soft and hard contact surfaces. A disinfectant may comprise, consists essentially of or consist of water having a pH of more than 11, wherein the disinfectant consists essentially of water having a pH of 11 when there are not more than 2% of other compounds, other than water, and preferably, no more than 1% other compounds. The disinfecting 24 also includes a disinfectant that may include a wide variety of EPA and/or FDA registered and approved disinfectant, which may be a non-rinse disinfectants and sanitizers to eliminate bacteria, fungi, viruses and algae within a wide range of these individual module units. This disinfecting system may be configured for a wide variety of enclosures, or individual module unit(s), including, but not limited to, subways, buses, airplanes and other public transportation, which require surface disinfecting. within the interior of the enclosure, such as onto the surfaces within the interior of the enclosure. There are other types of individual module unit(s), intermodal and/or static, which may require the disinfectant to include a cleanser, such as a soap the system may include nozzles that produce a high-pressure stream of disinfectant, such as in a power wash application; such as for, portable toilets, refrigerated and/or non-refrigerated shipping containers. Furthermore, enclosures may be refrigerated and/or non-refrigerated shipping containers. An exemplary disinfecting system may dispense or apply Ethylene, Ozone, Oxygen gases within the enclosure.

In addition, the high pressure fluid delivery unit 300 requires an on/off flow control valve 60 and the fluid manifold 402 are both required for a solo and separate flow of a single fluid. A fluid filter 404 is required to mitigate any particulate matter or hard water from clogging the static unit delivery systems components, such as the valves or nozzles. The pump 300B creates the pressurization for the disinfectant 24 and forces the disinfectant 24 through the distribution conduit in a direction of flow 202. A water source 108 may be used with the preparation of the disinfectant, especially when the disinfectant is produced by the system. The disinfectant may be produced and stored in disinfectant storage tanks 308. A second tank may comprise a rinse solution or dispersant 306 that may include water and may be combined with the disinfectant 24. The system may be configured to dispense a disinfectant solution that includes the disinfectant combined with a dispersant. In addition, the system may be configured to dispense a washing fluid, which may include the dispersant into an enclosure to rinse and/or wash the enclosure.

Figure 2:
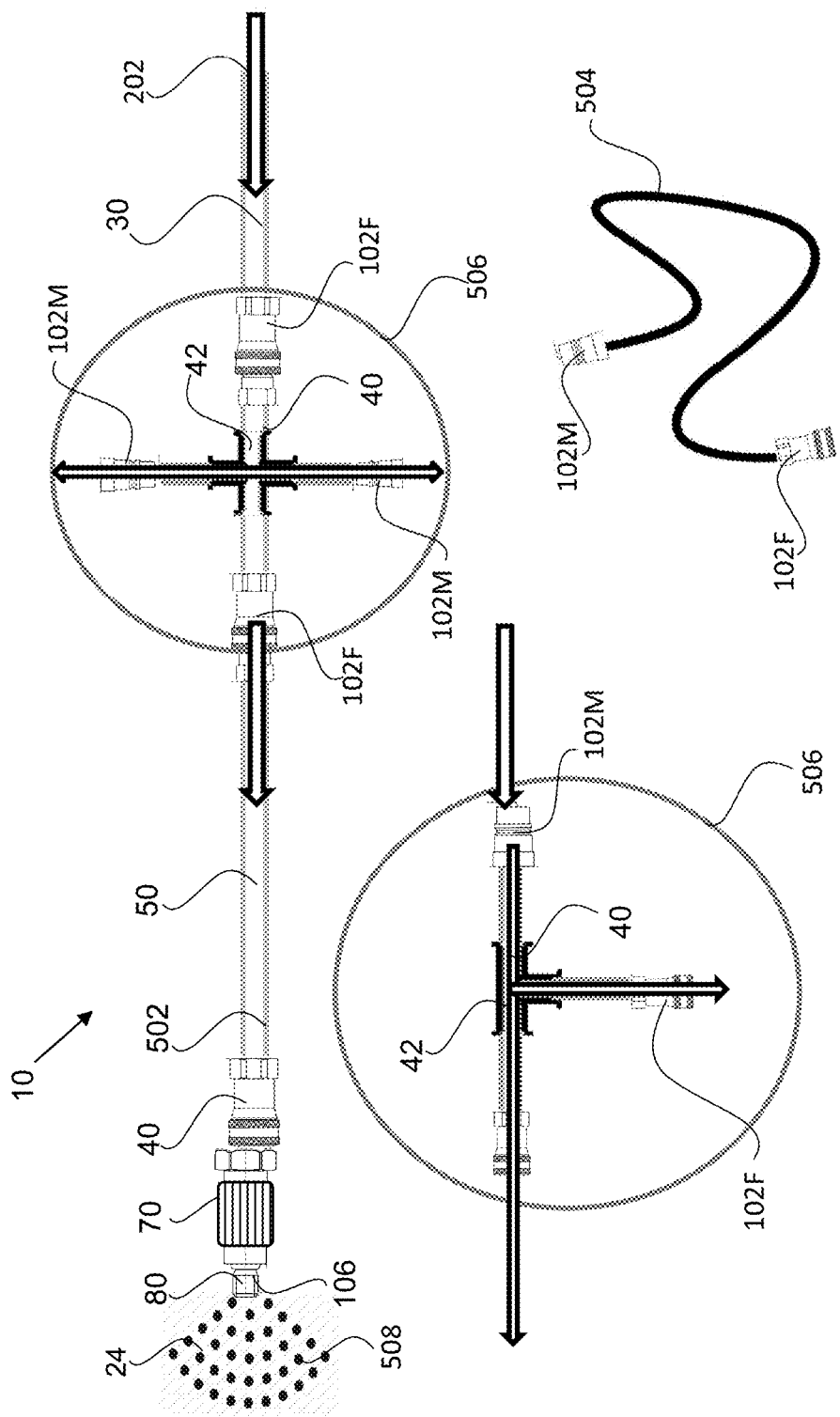
FIG. 2 shows an exemplary external primary and secondary high pressure delivery valve coupling hose(s), unit(s) connectivity routing configuration components

As shown in FIG. 2, an exemplary disinfecting system 10 comprises a distribution conduit 30 that extends from a disinfectant source. The disinfectant flows in a flow direction 202 through the distribution conduit to the coupling 40, which may be branched coupling 42, having two or more couplings extending from the distribution conduit. A delivery conduit 50 is coupled to the distribution conduit 30 by a coupling 40. The delivery conduit may have a coupling 40 for quick detachable attachment of a dispense port 70 which may include a nozzle 80, such as an atomizing nozzle 106, for dispensing the disinfectant 24, such as an atomized disinfectant 508A. A coupling may be a branched coupling 42 having three or four conduits coupled to the branched coupling.

FIG. 2. illustrates the external primary external fluid delivery hose 502, the secondary external fluid delivery hose 504 and the external hose and hardware. The distribution and/or delivery conduits may be high pressure fluid delivery conduits, or hoses, and may be flexible. These fluid coupling lines may be quickly connectable connect couplings, such as a male connect coupling 102M and a female connect coupling 102F.

Figure 3:
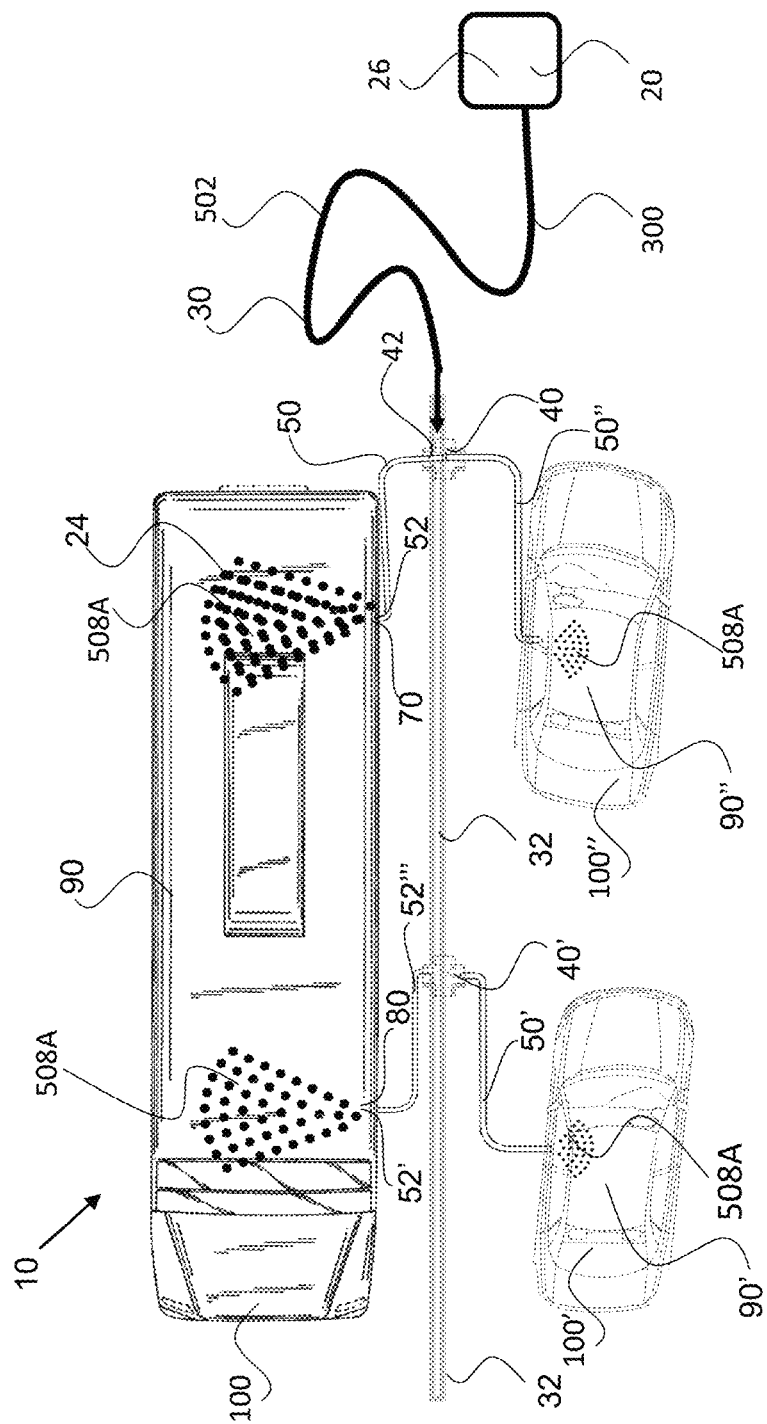
FIG. 3 shows top view of an exemplary disinfecting system configured with delivery conduits extending from a distribution conduit to a bus and two automobiles.

As shown in FIG. 3 an exemplary disinfecting system 10 is configured to sanitize a plurality of enclosures 90-90", including a bus enclosure 90 and two automobile enclosures 90', 90". The distribution conduit 30 extends from a disinfectant source 20 and provides a flow of disinfectant 24. A coupling 40, which is a branched coupling, enables delivery conduits 50-50" to be coupled to the distribution conduit. A spray of disinfectant 24 is dispensed within the enclosures. A distribution conduit extension 32, or an extension from a first coupling 40 extends to a second coupling 40', wherein two addition delivery conduits are coupled. The bus may have an integrated deliver portion 52, wherein the dispense port 70 and nozzle 80 are fixed to the bus and require coupling with the delivery conduit to enable dispensing the disinfectant into the bus. The bus may have a quick connect coupling 40 that is part of the integrated deliver portion.

FIG. 3 shows an autonomous high pressure fluid delivery unit 300, configured for pumping a disinfecting solution 26, for treatment, the individual delivery units 100, or enclosures 90-90" include a school bus and two cars. The primary external fluid delivery hose 502, delivers the disinfecting solution 26 to the coupling 40, that branches into a distribution conduit extensions 32 and two delivery conduits 50, 50'. The delivery conduit 50 is coupled with an integrated deliver portion 52, that is attached with the bus and configured for coupling, such as with a quick connecting coupling, to the deliver conduit. The delivery conduits 50' and 50" extend to the automobiles, or cars and may terminate or couple with a window adapter 76, as shown in FIG. 5, to couple the delivery conduit to the window of the automobile. The window adaptor is an example of an integrated delivery portion 52, but is not a fixed integrated delivery portion that is affixed to the enclosure. The window adaptor is configured for temporary detachable attachment to the window of an automobile. The distribution conduit extension 32 extends from the coupling 40 to a second coupling 40' that again has two deliver conduits 50' and 50", to the second automobile and to a second integrated deliver port 52' coupled with the bus. A second distribution conduit extension extends from the second coupling 40' and may extend to additional couplings that have deliver conduits coupled thereto. A plurality of vehicle enclosures may be disinfected quickly with this system, such as at a rental car facility or municipal transit station. The disinfecting solution 26 may be dispensed as a dry fog including an atomized disinfectant 508A, or atomized disinfecting solution, as shown.

Referring now to FIGS. 4 and 5, an exemplary disinfecting system 10 is configured for delivery of disinfectant 24 into an automobile 92 via a window adapter 76. The window adapter has a channel 79 for receiving the top of the window and a seal portion 77 for sealing off the window. The window adapter has an adapter conduit 78 that extends through the seal portion to enable a flow of disinfectant through the window adapter. The adapter conduit extends between the valve 60 and the dispense port 70 and across the window adapter 76. The window adapter is coupled with a delivery conduit 50 and a control valve 60 may be configured proximal to the window adapter to enable control of the flow of disinfectant into the vehicle. On the inside surface of the window adapter the dispense port 70 comprises a nozzle 80 to produce a spray of disinfectant 24. The nozzle may be an atomizing nozzle 106 that is configured to produce an atomized disinfectant 508A of into the enclosure. The dry fog may have a very small particle size such as no more than 25 micron, no more than 10 micron, no more than 5 micron and any range between and including the particle sizes provided.

Figure 6:
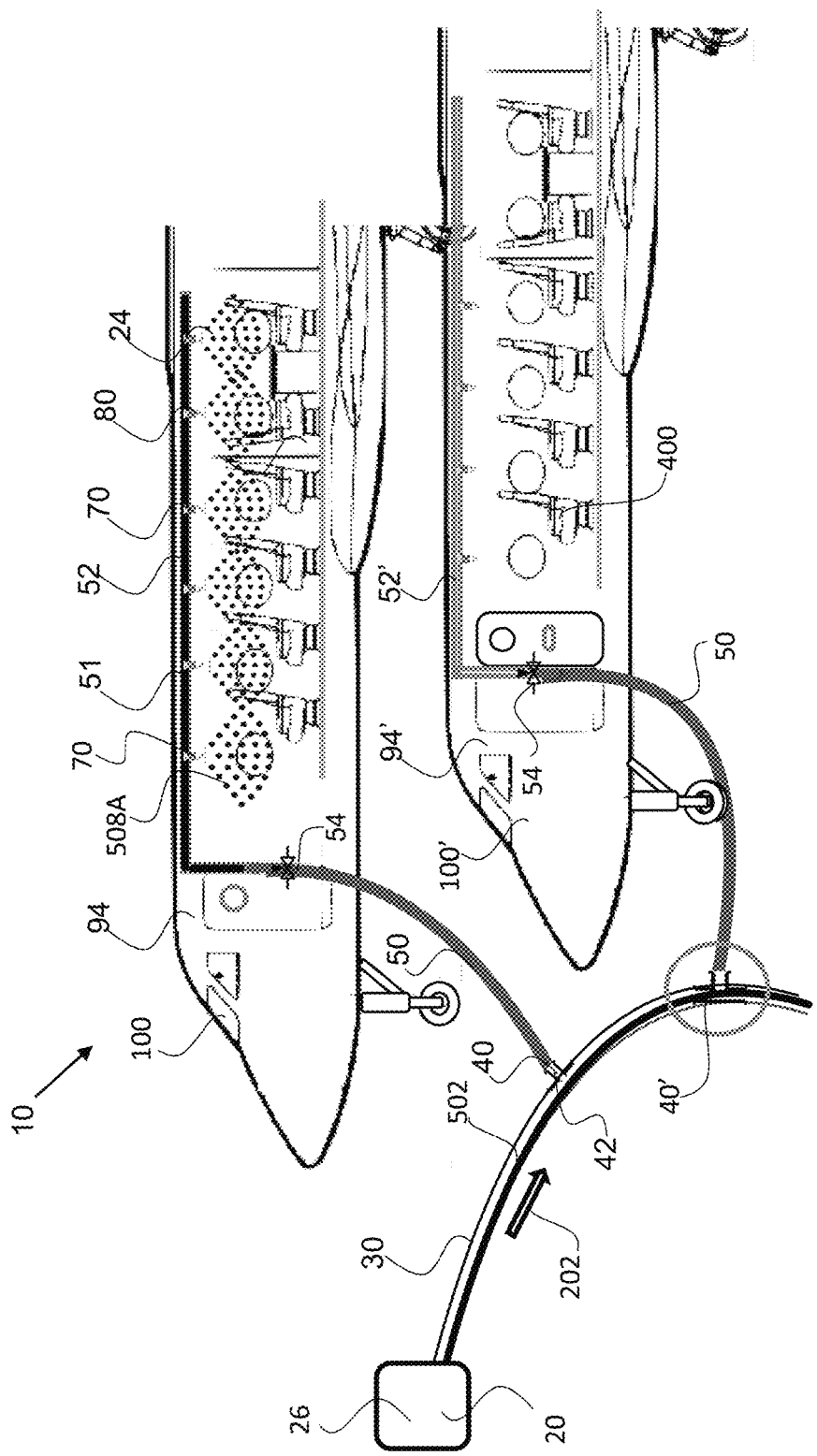
FIG. 6 shows a side view of two aircrafts having an integrated deliver portion coupled with a distribution conduit to sanitize the interior of the aircraft between flights.

As shown in FIG. 6, an exemplary disinfecting system 10 is configured for delivery of disinfectant 24 into a plurality of aircraft, two airplanes 94, 94' as shown. The distribution conduit 30 extends from the disinfectant source 20, which may be a tank for retaining a disinfecting solution 26. The deliver conduit extends to a plurality of couplings 40, 40' that extend to delivery conduits. A coupling 40" The delivery conduits extend to an integrated delivery coupling 54. Each of the airplanes has an integrated deliver portion 52, 52', comprising an integrated delivery conduit 51 that extends from an integrated coupling 54 to the plurality of dispense ports 70, comprising a nozzle 80 for dispensing the disinfectant 24 into the airplane. Note that each of the integrated delivery portions comprises a plurality dispense ports to enable effective disinfecting of the interior of the airplane. Any number of dispense ports may be coupled with the integrated delivery conduit to ensure effective disinfection down the length of the airplane cabin. A dispense port may be configured over each set of seats on either side of the aisle or configured over every seat 400. The disinfectant flow through the distribution conduit 30 to coupling 40, wherein a delivery conduit 50 extend from the coupling to the integrated coupling 54. With this system, airplanes can be sanitized quick between flights by simple coupling the delivery conduit with the integrated coupling and turning on a valve to begin the flow of disinfectant. The disinfectant may be a gas, such as ethylene or ozone, or may a solution.

Figures 7, 8:
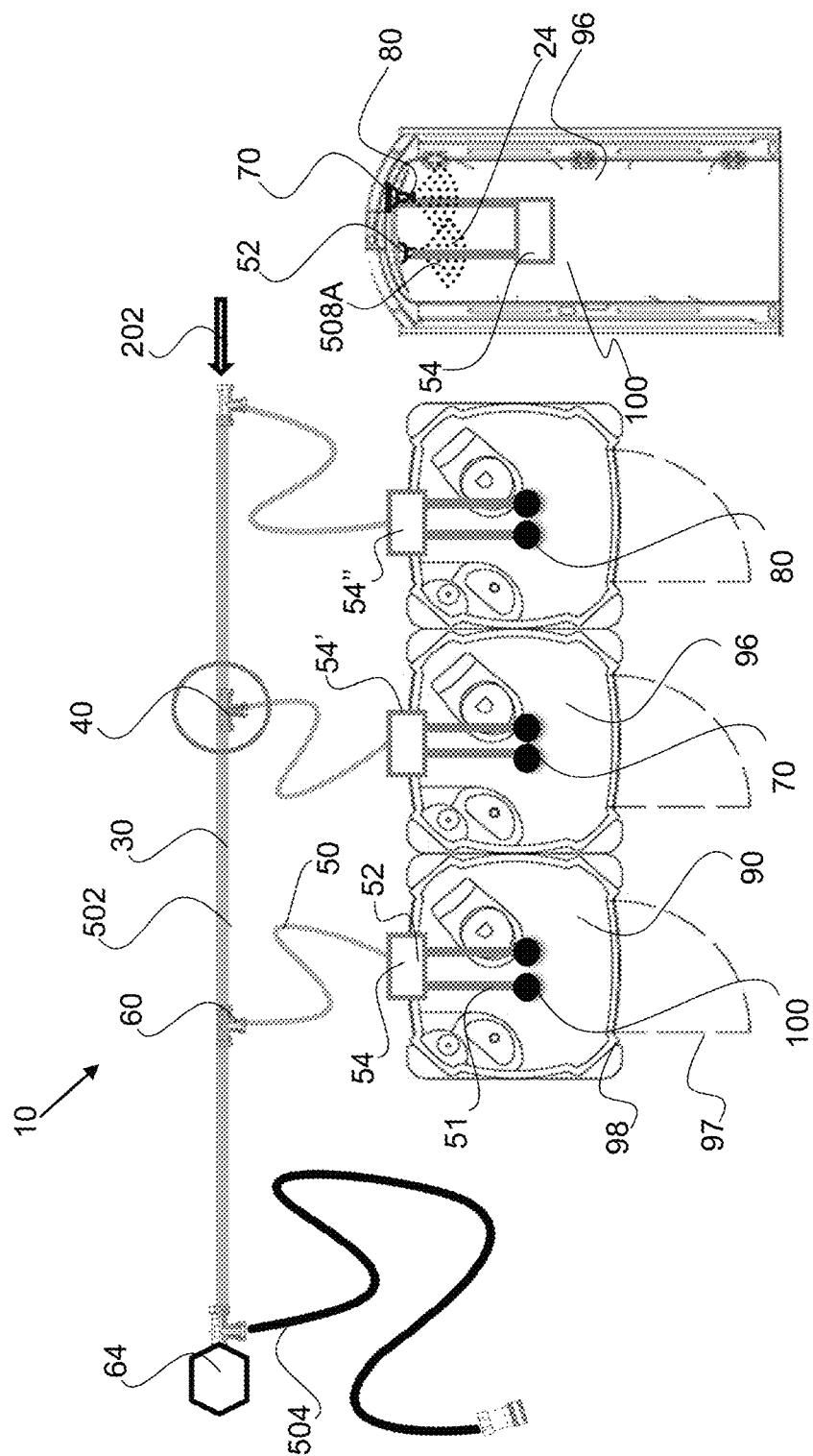
FIG. 7 shows a top view of a plurality of lavatories coupled with a disinfecting system to sanitize the interior of the lavatory.
FIG. 8 shows a front view of a lavatory with the door open.

Referring now to FIGS. 7 and 8, an exemplary disinfecting system 10 is configured for delivery of disinfectant 24 into a plurality of lavatories, or portable toilets 96. A distribution conduit 30 extends and has a plurality of couplings 40 for coupling a delivery conduit 50 to the enclosure 90. The portable toilets may have an integrated delivery portion 52 that includes the dispensing port 70 and nozzle 80. An integrated coupling 54 may enable quick connection of the delivery conduit 50 to the integrated delivery portion and a integrated delivery conduit 51 may extend from the integrated coupling to the dispense port 70 and nozzle 80. A door sensor 98 may sense the position of a door 97 and provide a signal to a controller 64 that controls the opening and closing of valves to each lavatory. A secondary external delivery hose may be used for manual dispensing disinfectant into the portable toilets or another enclosure. Again, the disinfectant 24 may be dispensed from the nozzle 80 as an atomized disinfectant 508A.

Referring now to FIGS. 9 and 10, an exemplary disinfecting system comprises a distribution conduit 30 that is coupled with a delivery conduit 50 by a coupling 40 and a control valve 60 to control the flow of disinfectant to a dispense port 70 having a nozzle 80. In this embodiment, two distribution conduits 30, 30' are coupled with a single delivery conduit 50 to enable the delivery of a disinfectant, such as a soap solution or cleanser through distribution conduit 30 and then the delivery of a rinse solution, such as water or a water solution through distribution conduit 30'. This type of system may be used for disinfecting a shipping container 99, wherein the interior is washed and then rinsed. Note that the shipping container may have an integrated delivery portion 52 comprising an integrated delivery conduit 51, a dispensing portion 70 and nozzle 80. The valve 60 may be an electronic valve 604 that is controlled by a controller to open and close without manual intervention with the valve. The electronic valve may comprise a wireless signal receiver 605 that receives a wireless signal to open and/or close the valve as required. This arrangement may allow the enclosure to be cleaned under a protocol and allow the disinfectant and/or cleaning and rinsing fluids to be dispensed in a required order for a required period of time.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A disinfecting system for disinfecting a plurality of enclosures comprising:
   a) said plurality of enclosures wherein said plurality of enclosures are separate enclosures;
   b) a single disinfectant source (26) for containing a disinfectant (24);
   c) a single pump for distributing the disinfectant from the fluid source to each of the plurality of enclosures;
   d) a distribution conduit (30) coupled with the disinfectant source;
   e) a plurality of couplings (40) configured on the distribution conduit;
   f) a plurality of delivery conduits (50), each coupled to the distribution conduit by one of said plurality of couplings;
      wherein each delivery conduit of said plurality of delivery conduits extends from the one of said plurality of couplings to one of the plurality of enclosures;
      wherein each of the delivery conduits is detachably attachable to the distribution conduit:
   g) a dispensing port (70) coupled with each delivery conduit and configured to dispense the disinfectant into one of said plurality of enclosures;
   h) a control valve (60) configured to allow a flow of said disinfectant through the disinfecting system;
   i) an integrated disinfecting portion that is coupled with the enclosure and having an integrated coupling configured for detachable attachment to the distribution conduit
   wherein the integrated disinfection portion is affixed to the enclosure and comprises an integrated delivery conduit extending from the integrated coupling to the dispensing port.

2. The disinfecting system of claim 1, wherein the integrated disinfection portion is detachably attached to the enclosure.

3. The disinfecting system of claim 2, wherein the enclosure comprises an automobile and wherein the integrated disinfecting portion comprises a window adapter.

4. The disinfecting system of claim 3, wherein the window adapter comprises a channel configured extend over a window of an automobile.

5. The disinfecting system of claim 4, wherein the window adapter comprises an adapter conduit configured between the delivery conduit and the dispense port.

6. The disinfecting system of claim 1, wherein the enclosure comprises an aircraft.

7. The disinfecting system of claim 1, wherein the enclosure comprises a lavatory.

8. The disinfecting system of claim 1, wherein the enclosure comprises a shipping container.

9. The disinfecting system of claim 1, wherein the control valve comprises a wireless receiver and wherein the valve is controlled by a wireless signal.

10. The disinfecting system of claim 1, wherein the control valve is configured between the distribution conduit and at least one of the plurality of delivery conduits.

11. The disinfecting system of claim 1, wherein the disinfectant comprises Hypochlorous Acid (HOCl).

12. The disinfecting system of claim 11, wherein the disinfectant port is configured to dispense the disinfectant as a dry-fog micro droplet.

13. The disinfecting system of claim 1, wherein the disinfectant comprises ethylene.

14. The disinfecting system of claim 1, wherein the disinfectant comprises a dry gas.

15. The disinfecting system claim 1, wherein the disinfectant port comprises an atomizing nozzle.

16. The disinfecting system claim 1, further comprising a controller that is coupled with the valve to control the flow of disinfectant to the dispensing port.

17. The disinfecting system of claim 1, wherein the disinfectant consists essentially of water having a pH of greater than 11.

* * * * *